(12) United States Patent
Nakazawa

(10) Patent No.: US 8,309,753 B2
(45) Date of Patent: Nov. 13, 2012

(54) METHOD FOR PRODUCING OPTICALLY ACTIVE CYANOHYDRIN COMPOUND

(75) Inventor: Koichi Nakazawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 88 days.

(21) Appl. No.: 12/936,340

(22) PCT Filed: Apr. 3, 2009

(86) PCT No.: PCT/JP2009/057302
§ 371 (c)(1), (2), (4) Date: Oct. 4, 2010

(87) PCT Pub. No.: WO2009/128390
PCT Pub. Date: Oct. 22, 2009

(65) Prior Publication Data
US 2011/0034718 A1    Feb. 10, 2011

(30) Foreign Application Priority Data
Apr. 18, 2008   (JP) ................. 2008-108772

(51) Int. Cl.
C07C 253/00    (2006.01)
C07F 5/06    (2006.01)

(52) U.S. Cl. .......................... 558/351; 546/10

(58) Field of Classification Search .................. None
See application file for complete search history.

(56) References Cited

U.S. PATENT DOCUMENTS
5,003,083 A    3/1991 Inoue et al.
6,248,918 B1*    6/2001 Shibasaki et al. ............. 558/315
2004/0171862 A1    9/2004 Kirschbaum et al.

FOREIGN PATENT DOCUMENTS
JP    63-150256 A    6/1988
WO    WO01/38554 A2 *    5/2001

OTHER PUBLICATIONS

Aspinall et al., "Catalytic, Asymmetric Cyanohydrin Synthesis Mediated by Lanthanide (III) Chloride Pybox Complexes", Tetrahedron Letters, 1999, vol. 40, pp. 1763-1766.

Aspinall et al., "Lanthanide complexes with C2 symmetric ligands for use in enantioselective organic synthesis", Journal of Alloys and Compounds, 2000, vol. 303-304, pp. 173-177.
International Search Report—dated May 19, 2009 for PCT/JP2009/057302.
Iovel et al., "Trimethylsilylcyanation of aromatic aldehydes catalyzed by Pybox-AlCl3 complex", Tetrahedron: Assymmetry, 1997, vol. 8, No. 8, pp. 1279-1285.
English translation of International Preliminary Report on Patentability (Form PCT/IB/338 and 373) and of Written Opinion of the international Searching Authority (Form PCT/ISA/237) mailed Dec. 9, 2010 in international Application No. PCT/JP2009/057302.

* cited by examiner

*Primary Examiner* — Kamal Saeed
*Assistant Examiner* — Nyeemah A Grazier
(74) *Attorney, Agent, or Firm* — Birch, Stewart, Kolasch & Birch, LLP

(57) ABSTRACT

A method of producing an optically active cyanohydrin compound represented by formula (3), which includes reacting an aldehyde compound represented by formula (2) with hydrogen cyanide in the presence of a silyl compound and an asymmetric complex which is obtained by reacting an optically active pyridine compound represented by formula (1) with an aluminum halide, and wherein $Q^1$, $Q^2$, $R^1$ and $R^2$ are defined in the specification.

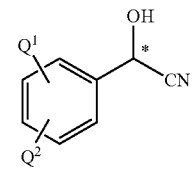

(3)

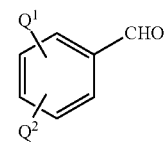

(2)

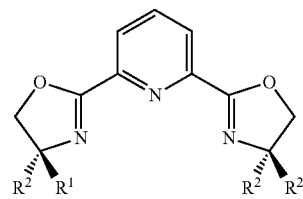

(1)

9 Claims, No Drawings

METHOD FOR PRODUCING OPTICALLY ACTIVE CYANOHYDRIN COMPOUND

TECHNICAL FIELD

The present invention relates to a method of producing an optically active cyanohydrin compound.

BACKGROUND TECHNOLOGY

U.S. Pat. No. 4,503,071 discloses that optically active m-phenoxy-mandelonitrile is used as a production intermediate of an agricultural fungicide.

Optically active m-phenoxy-mandelonitrile is one of optically active cyanohydrin compounds, and as a method of producing an optically active cyanohydrin compound, known is a method which comprises reacting an aldehyde with hydrogen cyanide in the presence of an optically active vanadyl catalyst (see, Japanese Patent Application National Publication (Laid-Open) No. 2004-533490). Meanwhile, there is also known a method in which aluminum chloride and an optically active bisoxazolylpyridine compound are reacted to obtain an asymmetric complex, and an aldehyde compound and trimethylsilyl cyanide are reacted in the presence of this asymmetric complex to produce an O-silyl ether of an optically active cyanohydrin compound (see, Tetrahedron: Asymmetry, Vol. 8, p. 1279 (1997)).

DISCLOSURE OF THE INVENTION

The present invention provides the following <1> to <11>.

<1> A method of producing an optically active cyanohydrin compound represented by formula (3)

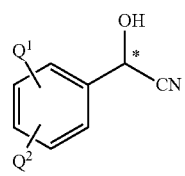

(3)

(wherein, $Q^1$ and $Q^2$ are as defined below, and * represents that the indicated carbon atom is the optically active center) comprising reacting an aldehyde compound represented by formula (2)

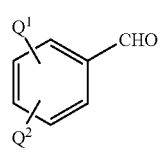

(2)

(wherein, $Q^1$ and $Q^2$ represent each independently a hydrogen atom, optionally substituted alkyl group having 1 to 6 carbon atoms, optionally substituted alkoxy group having 1 to 4 carbon atoms, acyloxy group having 2 to 8 carbon atoms, optionally substituted alkanesulfonyloxy group having 1 to 4 carbon atoms, optionally substituted benzenesulfonyloxy group, trialkylsilyloxy group having 1 to 10 carbon atoms or optionally substituted aryloxy group having 6 to 10 carbon atoms) with hydrogen cyanide in the presence of a silyl compound and an asymmetric complex which is obtained by reacting an optically active pyridine compound represented by formula (1)

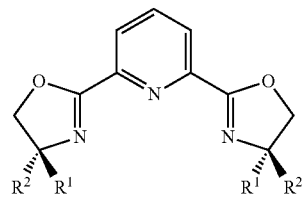

(1)

(wherein, $R^1$ and $R^2$ represent each independently a hydrogen atom, alkyl group having 1 to 6 carbon atoms, aryl group having 6 to 10 carbon atoms or aralkyl group having 7 to 11 carbon atoms, provided that $R^1$ and $R^2$ are not the same.) with an aluminum halide;

<2> The production method according to <1> wherein the silyl compound is a trialkylsilyl cyanide compound;

<3> The production method according to <1> wherein the silyl compound is trimethylsilyl cyanide;

<4> The production method according to any one of <1> to <3> wherein the aluminum halide is aluminum chloride;

<5> The production method according to any one of <1> to <4> wherein either $R^1$ or $R^2$ is a hydrogen atom and the other is an alkyl group having 1 to 6 carbon atoms, aryl group having 6 to 10 carbon atoms or aralkyl group having 7 to 11 carbon atoms;

<6> The production method according to any one of <1> to <4> wherein either $R^1$ or $R^2$ is a hydrogen atom and the other is an alkyl group having 1 to 6 carbon atoms or aryl group having 6 to 10 carbon atoms;

<7> The production method according to any one of <1> to <6> wherein $Q^1$ represents a hydrogen atom and $Q^2$ represents an optionally substituted alkyl group having 1 to 6 carbon atoms, optionally substituted alkoxy group having 1 to 4 carbon atoms, acyloxy group having 2 to 8 carbon atoms, optionally substituted alkanesulfonyloxy group having 1 to 4 carbon atoms, optionally substituted benzenesulfonyloxy group, trialkylsilyloxy group having 1 to 10 carbon atoms or optionally substituted aryloxy group having 6 to 10 carbon atoms;

<8> The production method according to any one of <1> to <6> wherein $Q^1$ represents a hydrogen atom and $Q^2$ represents an optionally substituted alkyl group having 1 to 6 carbon atoms or optionally substituted aryloxy group having 6 to 10 carbon atoms;

<9> The production method according to any one of <1> to <8> wherein the use amount of the asymmetric complex is 0.005 to 1 mol, in terms of aluminum atom, with respect to 1 mol of the aldehyde compound represented by formula (2);

<10> The production method according to any one of <1> to <9> wherein the use amount of the silyl compound is 0.01 to 0.5 mol with respect to 1 mol of the aldehyde compound represented by formula (2);

<11> The production method according to any one of <1> to <10> wherein the use amount of hydrogen cyanide is 1.1 to 3 mol with respect to 1 mol of the aldehyde compound represented by formula (2).

BEST MODES FOR CARRYING OUT THE INVENTION

The aluminum halide includes aluminum chloride and aluminum bromide, and aluminum chloride is preferable. Commercially available aluminum halides may be used, and aluminum halides produced according to known methods may also be used.

In the formula of the optically active pyridine compound represented by formula (1)

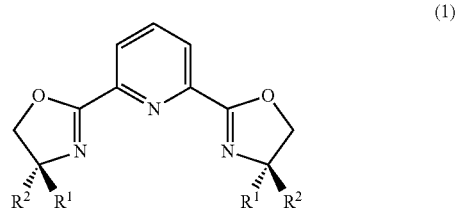

(1)

(hereinafter, abbreviated as optically active pyridine compound (1)), $R^1$ and $R^2$ represent each independently a hydrogen atom, alkyl group having 1 to 6 carbon atoms, aryl group having 6 to 10 carbon atoms or aralkyl group having 7 to 11 carbon atoms, provided that $R^1$ and $R^2$ are not the same.

The alkyl group having 1 to 6 carbon atoms includes a methyl group, ethyl group, propyl group, butyl group, pentyl group, hexyl group, isopropyl group, isobutyl group, sec-butyl group and tert-butyl group, and alkyl groups having 1 to 4 carbon atoms are preferable.

The aryl group having 6 to 10 carbon atoms includes a phenyl group and naphthyl group, and a phenyl group is preferable.

The aralkyl group having 7 to 11 carbon atoms includes a benzyl group and naphthylmethyl group.

Optically active pyridine compounds (1) in which either $R^1$ or $R^2$ is a hydrogen atom and the other is an alkyl group having 1 to 6 carbon atoms, aryl group having 6 to 10 carbon atoms or aralkyl group having 7 to 11 carbon atoms are preferable, and optically active pyridine compounds (1) in which either $R^1$ or $R^2$ is a hydrogen atom and the other is an alkyl group having 1 to 6 carbon atoms or aryl group having 6 to 10 carbon atoms are more preferable.

The optically active pyridine compound (1) includes optically active 2,6-bis(4-methyloxazol-2-yl)pyridine, optically active 2,6-bis(4-ethyloxazol-2-yl)pyridine, optically active 2,6-bis(4-isopropyloxazol-2-yl)pyridine, optically active 2,6-bis(4-tert-butyloxazol-2-yl)pyridine, optically active 2,6-bis(4-sec-butyloxazol-2-yl)pyridine, optically active 2,6-bis(4-isobutyloxazol-2-yl)pyridine, optically active 2,6-bis(4-phenyloxazol-2-yl)pyridine, optically active 2,6-bis(4-naphthyloxazol-2-yl)pyridine, optically active 2,6-bis(4-benzyloxazol-2-yl)pyridine and optically active 2,6-bis[4-(naphthylmethyl)oxazol-2-yl]pyridine.

Such an optically active pyridine compound (1) may be an S isomer or R isomer. Such a mixture may be used as a mixture of an S isomer and a R isomer, either isomer of which is contained in a larger amount than that of the other.

As the optically active pyridine compound (1), commercially available compounds may be used, and compounds produced according to known methods described in JP-A Hei 2-36181 and the like may also be used.

The use amount of the optically active pyridine compound (1) is usually 0.8 to 5 mol, preferably 1 to 2 mol with respect to 1 mol of an aluminum halide.

By reacting an aluminum halide with an optically active pyridine compound (1), an asymmetric complex is obtained. Such a reaction is usually carried out in the presence of a solvent.

The solvent includes halogenated hydrocarbon solvents such as dichloromethane, 1,2-dichloromethane and chloroform, and aromatic hydrocarbon solvents such as benzene, toluene, xylene, chlorobenzene and dichlorobenzene. Thought the use amount of the solvent is not restricted, it is usually 10 to 500 parts by weight with respect to 1 part by weight of the aluminum halide.

Such a reaction is carried out preferably in the absence of water. It is preferable to carry out the reaction under an atmosphere of an inert gas such as argon and nitrogen.

The reaction temperature is usually −20° C. or more, preferably 5 to 50° C. In the case that an aromatic hydrocarbon is used as the solvent, it is preferable to carryout the reaction at 50° C. or less from the standpoint of suppressing progress of side reactions.

The reaction time is usually 1 minute to 5 hours.

Thus, a mixture containing an asymmetric complex is obtained, and the resultant mixture may be used directly in a reaction of aldehyde compound represented by formula (2) and hydrogen cyanide to be described later, or the asymmetric complex taken out from the mixture by isolation means such as concentration may be used. Usually, the resultant mixture containing the asymmetric complex is used directly for the reaction of aldehyde compound represented by formula (2) with hydrogen cyanide.

In the formula of aldehyde compound represented by formula (2)

(2)

(hereinafter, abbreviated as aldehyde compound (2))

$Q^1$ and $Q^2$ represent each independently a hydrogen atom, optionally substituted alkyl group having 1 to 6 carbon atoms, optionally substituted alkoxy group having 1 to 4 carbon atoms, optionally substituted acyloxy group having 2 to 8 carbon atoms, optionally substituted alkanesulfonyloxy group having 1 to 4 carbon atoms, optionally substituted benzenesulfonyloxy group, trialkylsilyloxy group having 1 to 10 carbon atoms or optionally substituted aryloxy group having 6 to 10 carbon atoms.

The alkyl group having 1 to 6 carbon atoms includes a methyl group, ethyl group, propyl group, isopropyl group, butyl group, isobutyl group, tert-butyl group, pentyl group and hexyl group.

Such an alkyl group may be substituted by at least one substituent, and the substituent includes alkoxy groups having 1 to 4 carbon atoms such as a methoxy group, ethoxy group, propoxy group and butoxy group; alkylthio groups having 1 to 4 carbon atoms such as a methylthio group, ethylthio group, propylthio group and butylthio group; aryloxy groups having 6 to 12 carbon atoms such as a phenoxy group and 2,5-dimethylphenoxy group; arylthio groups having 6 to 12 carbon atoms such as a phenylthio group and 2,5-dimethylphenylthio group; alkylsulfonyl groups having 1 to 4 carbon atoms optionally substituted by a halogen atom such as a methanesulfonyl group, trifluoromethanesulfonyl group and chloromethanesulfonyl group; benzenesulfonyl groups optionally substituted by a nitro group or an alkyl group having 1 to 4 carbon atoms such as a benzenesulfonyl group, p-toluenesulfonyl group and o-nitrobenzenesulfonyl group.

The alkyl groups substituted by such a substituent include a methoxymethyl group, ethoxymethyl group, methylthiomethyl group, phenylthiomethyl group, 2,5-dimethylphenoxymethyl group, methanesulfonylmethyl group, chloromethanesulfonylmethyl group, trifluoromethanesulfonylmethyl group, benzenesulfonylmethyl group, 4-methylbenzenesulfonylmethyl group, 4-nitrobenzenesulfonylmethyl group, 2-methoxyethyl group, 2-ethoxyethyl group, 2-(methylthio)ethyl group, 2-(phenylthio)ethyl group, 2-methanesulfonylethyl group, 2-trifluoromethanesulfonylethyl group, 2-benzenesulfonylethyl group and 2-(4-nitrobenzenesulfonyl)ethyl group.

The alkoxy group having 1 to 4 carbon atoms includes the same groups as described above. Such an alkoxy group may be substituted by at least one substituent, and the substituent includes halogen atoms such as a fluorine atom.

The alkoxy groups substituted by such a substituent include a difluoromethoxy group, trifluoromethoxy group, pentafluoroethoxy group and 1,1,1,3,3,3-hexafluoro-2-propoxy group.

The acyloxy group having 2 to 8 carbon atoms includes an acetoxy group, propionyloxy group, butyryloxy group, pivaloyloxy group, neopentanecarbonyloxy group, benzoyloxy group, phenylacetoxy group and naphthylacetoxy group.

The alkanesulfonyloxy group having 1 to 4 carbon atoms includes a methanesulfonyloxy group. Such an alkanesulfonyloxy group may be substituted by at least one substituent, and the substituent includes halogen atoms such as a fluorine atom. The alkanesulfonyloxy groups substituted by such a substituent include a trifluoromethanesulfonyloxy group.

The optionally substituted benzenesulfonyloxy group includes a benzenesulfonyloxy group, benzenesulfonyloxy groups substituted by an alkyl group having 1 to 4 carbon atoms such as a p-toluenesulfonyloxy group; benzenesulfonyloxy groups substituted by a nitro group such as an o-nitrobenzenesulfonyloxy group and p-nitrobenzenesulfonyloxy group.

The trialkylsilyloxy group having 1 to 10 carbon atoms includes a trimethylsilyloxy group, triethylsilyloxy group, tripropylsilyloxy group and tert-butyldimethylsilyloxy group.

The aryloxy group having 6 to 10 carbon atoms includes a phenoxy group and naphthyloxy group. Such an aryloxy group may be substituted by at least one substituent, and the substituent includes alkyl groups having 1 to 4 carbon atoms, alkoxy groups having 1 to 4 carbon atoms and halogen atoms. The aryloxy groups substituted by such a substituent include a 4-methylphenoxy group, 2-methylphenoxy group, 2,4-dimethylphenoxy group, 2,4-di-tert-butylphenoxy group, 4-methoxyphenoxy group, 4-ethoxyphenoxy group, 2-fluorophenoxy group, 4-fluorophenoxy group and pentafluorophenoxy group.

Aldehyde compounds (2) in which $Q^1$ represents a hydrogen atom and $Q^2$ represents an optionally substituted alkyl group having 1 to 6 carbon atoms, optionally substituted alkoxy group having 1 to 4 carbon atoms, acyloxy group having 2 to 8 carbon atoms, optionally substituted alkanesulfonyloxy group having 1 to 4 carbon atoms, optionally substituted benzenesulfonyloxy group, trialkylsilyloxy group having 1 to 10 carbon atoms or optionally substituted aryloxy group having 6 to 10 carbon atoms are preferable, and aldehyde compounds (2) in which $Q^1$ represents a hydrogen atom and $Q^2$ represents an optionally substituted alkyl group having 1 to 6 carbon atoms or optionally substituted aryloxy group having 6 to 10 carbon atoms are more preferable.

The aldehyde compound (2) includes benzaldehyde,
o-methylbenzaldehyde, p-methylbenzaldehyde,
o-ethylbenzaldehyde, o-isopropylbenzaldehyde,
p-tert-butylbenzaldehyde, o-methoxymethylbenzaldehyde,
o-(2-methoxyethyl) benzaldehyde,
o-(ethoxymethyl) benzaldehyde,
o-(methylthiomethyl) benzaldehyde,
o-(2-methylthioethyl) benzaldehyde,
o-(ethylthiomethyl) benzaldehyde,
o-(phenoxymethyl)benzaldehyde,
o-(2,5-dimethylphenoxymethyl)benzaldehyde,
p-(2,5-dimethylphenoxymethyl)benzaldehyde,
o-(phenylthiomethyl)benzaldehyde,
o-(2,5-dimethylphenylthiomethyl)benzaldehyde,
o-methanesulfonylmethylbenzaldehyde,
o-trifluoromethanesulfonylmethylbenzaldehyde,
o-benzenesulfonylmethylbenzaldehyde,
o-(p-toluenesulfonylmethyl)benzaldehyde,
o-(o-nitrobenzenesulfonylmethyl)benzaldehyde,
o-methoxybenzaldehyde, m-methoxybenzaldehyde,
p-methoxybenzaldehyde, o-ethoxybenzaldehyde,
o-isopropoxybenzaldehyde, o-difluoromethoxybenzaldehyde,
o-trifluoromethoxybenzaldehyde,
o-pentafluoroethoxybenzaldehyde,
o-(1,1,1,3,3,3-hexafluoro-2-propoxy)benzaldehyde,
o-acetoxybenzaldehyde, p-acetoxybenzaldehyde,
o-propionyloxybenzaldehyde, o-butyryloxybenzaldehyde,
o-pivaloyloxybenzaldehyde, o-phenylacetoxybenzaldehyde,
p-phenylacetoxybenzaldehyde, o-naphthylacetoxybenzaldehyde,
o-methanesulfonyloxybenzaldehyde,
o-trifluoromethanesulfonyloxybenzaldehyde,
o-(p-toluenesulfonyloxy)benzaldehyde,
o-(o-nitrobenzenesulfonyloxy)benzaldehyde,
o-(p-nitrobenzenesulfonyloxy)benzaldehyde,
o-trimethylsilyloxybenzaldehyde,
o-triethylsilyloxybenzaldehyde,
o-tripropylsilyloxybenzaldehyde,
o-tert-butyldimethylsilyloxybenzaldehyde,
o-phenoxybenzaldehyde, m-phenoxybenzaldehyde,
o-naphthyloxybenzaldehyde, o-(4-methylphenoxy)benzaldehyde,
o-(2-methylphenoxy)benzaldehyde,
o-(2,4-dimethylphenoxy)benzaldehyde,
o-(2,4-di-tert-butylphenoxy)benzaldehyde,
o-(4-methoxyphenoxy)benzaldehyde,
o-(4-ethoxyphenoxy)benzaldehyde,
o-(2-fluorophenoxy)benzaldehyde,
o-(4-fluorophenoxy)benzaldehyde,
o-pentafluorophenoxybenzaldehyde,
o-(2,6-dimethylphenoxymethyl)-p-(methoxymethyl)benzaldehyde,
o-(2,6-dimethylphenoxymethyl)-p-(methylthiomethyl) benzaldehyde,
o-(2,6-dimethylphenoxymethyl)-p-(phenylthiomethyl) benzaldehyde,
o-(2,6-dimethylphenoxymethyl)-p-trifluoromethoxybenzaldehyde,
o-(2,6-dimethylphenoxymethyl)-p-pentafluoroethoxybenzaldehyde, o-(2,6-dimethylphenoxymethyl)-p-acetoxybenzaldehyde, o-(2,6-dimethylphenoxymethyl)-p-benzoyloxybenzaldehyde, o-(2,6-dimethylphenoxymethyl)-p-trimethylsilyloxybenzaldehyde, o-(2,6-dimethylphenoxymethyl)-p-triethylsilyloxybenzaldehyde, o-(2,6-dimethylphenoxymethyl)-p-(tert-butyldimethylsilyloxy)benzaldehyde, o-(2,6-dimethylphenoxymethyl)-p-phenoxybenzaldehyde and o-(2,6-dimethylphenoxymethyl)-p-pentafluorophenoxybenzaldehyde.

As the aldehyde compound (2), commercially available compounds may be used, and compounds produced according to known methods may also be used.

As the hydrogen cyanide, commercially available compounds may be used, and compounds produced according to known methods may also be used.

Hydrogen cyanide in the form of gas may be used, and hydrogen cyanide in the form of liquid may be used. Further, a hydrogen cyanide solution obtained by dissolving hydrogen cyanide in a solvent may also be used. The solvent for dissolving hydrogen cyanide includes halogenated hydrocarbons such as dichloromethane, 1,2-dichloromethane and chloroform; aromatic hydrocarbons such as benzene, toluene, xylene, chlorobenzene and dichlorobenzene; ether solvents such as tert-butylmethylether, diethylether and tetrahydrofuran. The use amount of the solvent may advantageously be 1 part by weight or more with respect to 1 part by weight of hydrogen cyanide.

The use amount of hydrogen cyanide may advantageously be 1 mol or more, preferably 1.1 to 3 mol, with respect to 1 mol of aldehyde compound (2).

The use amount of an asymmetric complex is usually 0.001 mol or more, preferably 0.005 to 1 mol and more preferably 0.01 to 1 mol, in terms of aluminum atom, with respect to 1 mol of aldehyde compound (2).

The silyl compound includes trialkylsilyl halides such as trimethylsilyl chloride and triethylsilyl chloride; trialkylsilyl cyanides such as trimethylsilyl cyanide; silylamines such as hexamethyldisilazane and tris(trimethylsilyl)amine; and trialkylsilyl cyanides are preferable, and trimethylsilyl cyanide is more preferable.

The use amount of the silyl compound is usually 0.01 to 0.5 mol, preferably 0.05 to 0.2 mol, with respect to 1 mol of the aldehyde compound (2).

The reaction of aldehyde compound (2) with hydrogen cyanide is carried out usually in the presence of a solvent. The solvent includes aromatic hydrocarbon solvents such as xylene, toluene, chlorobenzene, o-dichlorobenzene and benzene; aliphatic hydrocarbon solvents such as pentane, hexane, heptane and cyclohexane; ether solvents such as tetrahydrofuran, diethyl ether, tert-butyl methyl ether, cyclopentyl methyl ether, halogenated hydrocarbon solvents such as dichloromethane, 1,2-dichloroethane and chloroform. These may be used each singly, or two or more of them may be mixed and used. Of them, halogenated hydrocarbon solvents are preferable, and dichloromethane is more preferable.

Thought the use amount of of a solvent is not restricted, it is preferably 100 parts by weight or less with respect to 1 part by weight of aldehyde compound (2) from the economical standpoint.

Such a reaction is carried out usually by mixing an asymmetric complex, a silyl compound, an aldehyde compound (2) and hydrogen cyanide, and the mixing sequence of them is not restricted. For example, an aldehyde compound (2) and a silyl compound may be added to a mixture containing an asymmetric complex adjusted to a given reaction temperature, followed by adding hydrogen cyanide thereto; or a mixture obtained by mixing an asymmetric complex, an aldehyde compound (2) and a silyl compound may be adjusted to a given reaction temperature, followed by adding hydrogen cyanide thereto. A silyl compound may be added to a mixture containing an asymmetric complex adjusted to a given reaction temperature, and then add an aldehyde compound (2) and hydrogen cyanide simultaneously in a concurrent fashion; or a mixture containing an asymmetric complex adjusted to a given reaction temperature may be added hydrogen cyanide and a silyl compound, followed by adding an aldehyde compound (2) thereto. A mixture obtained by mixing an asymmetric complex and hydrogen cyanide may be adjusted to a given reaction temperature, followed by adding an aldehyde compound (2) thereto; or an asymmetric complex and a silyl compound may be added to an aldehyde compound (2) adjusted to a given reaction temperature, followed by adding hydrogen cyanide thereto. A mixture obtained by mixing an aldehyde compound (2), an asymmetric complex and a silyl compound may be adjusted to a given reaction temperature, followed by adding hydrogen cyanide to the mixture; or hydrogen cyanide and a silyl compound may be added to an aldehyde compound (2) adjusted to a given reaction temperature, followed by an asymmetric complex thereto. A mixture obtained by mixing an aldehyde compound (2), hydrogen cyanide and a silyl compound may be adjusted to a given reaction temperature, followed by adding an asymmetric complex to the mixture; or a mixture obtained by mixing an aldehyde compound (2) and a silyl compound may be adjusted to a given reaction temperature, followed by adding to the mixture hydrogen cyanide and an asymmetric complex simultaneously in a concurrent fashion. Particularly, it is preferable that an aldehyde compound (2) and a silyl compound are added to a mixture containing an asymmetric complex adjusted to a given reaction temperature, followed by adding hydrogen cyanide thereto.

The reaction temperature of the reaction of aldehyde compound (2) with hydrogen cyanide is usually −80 to 50° C., and it is preferably 0 to 35° C. from the standpoint of the yield and the enantiomeric excess of the intended optically active cyanohydrin compound represented by formula (3) (hereinafter, abbreviated as optically active cyanohydrin compound (3))

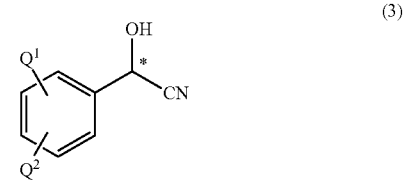

(3)

(wherein, $Q^1$ and $Q^2$ represent the same meaning as described above, and * represents that the indicated carbon atom is the optically active center).

Such a reaction maybe carried out under normal pressure, or may be carried out under positive pressure.

Progress of the reaction can be confirmed by usual analysis means such as gas chromatography, high performance liquid chromatography and NMR.

Thus, a reaction mixture containing an optically active cyanohydrin compound (3) is obtained, and for example, by washing the reaction mixture with water or an aqueous solution of an acid such as hydrochloric acid and concentrating the resultant organic layer, the optically active cyanohydrin compound (3) can be taken out. The taken out optically active cyanohydrin compound (3) may be further purified by usual purification means such as recrystallization, distillation and column chromatography.

Thus obtainable optically active cyanohydrin compound (3) includes optically active mandelonitrile, optically active o-methylmandelonitrile, optically active p-methylmandelonitrile, optically active o-ethylmandelonitrile, optically active o-isopropylmandelonitrile, optically active p-tert-butylmandelonitrile, optically active o-(methoxymethyl)mandelonitrile, optically active o-(2-methoxyethyl)mandelonitrile, optically active o-(ethoxymethyl)mandelonitrile, optically active o-(methylthiomethyl)mandelonitrile, optically active o-(2-methylthioethyl)mandelonitrile, optically active o-(ethylthiomethyl)mandelonitrile, optically active o-(phenoxymethyl)mandelonitrile, optically active o-(2,5-dimethylphenoxymethyl)mandelonitrile, optically active p-(2,5-dimethylphenoxymethyl)mandelonitrile, optically active o-(phenylthiomethyl)mandelonitrile, optically active o-(2,5-dimethylphenylthiomethyl)mandelonitrile, optically active o-(methanesulfonylmethyl)mandelonitrile, optically active o-(trifluoromethanesulfonylmethyl)mandelonitrile, optically active o-(benzenesulfonylmethyl)mandelonitrile, optically active o-(p-toluenesulfonylmethyl)mandelonitrile, optically active o-(o-nitrobenzenesulfonylmethyl)mandelonitrile, optically active o-methoxymandelonitrile, optically active m-methoxymandelonitrile, optically active p-methoxymandelonitrile, optically active o-ethoxymandelonitrile, optically active o-isopropoxymandelonitrile, optically active o-(difluoromethoxy)mandelonitrile, optically active o-trifluoromethoxymandelonitrile, optically active o-pentafluoroethoxymandelonitrile, optically active o-(1,1,1,3,3,3-hexafluoro-2-propoxy)mandelonitrile, optically active o-acetoxymandelonitrile, optically active p-acetoxymandelonitrile, optically active o-propionyloxymandelonitrile, optically active o-butyryloxymandelonitrile, optically active o-pivaloyloxymandelonitrile, optically active o-(phenylacetoxy)mandelonitrile, optically active p-(phenylacetoxy)mandelonitrile, optically active o-(naphthylacetoxy)mandelonitrile, optically active o-methanesulfonyloxymandelonitrile, optically active o-trifluoromethanesulfonyloxymandelonitrile, optically active o-(p-toluenesulfonyloxy)mandelonitrile, optically active o-(o-nitrobenzenesulfonyloxy)mandelonitrile, optically active o-(o-nitrobenzenesulfonyloxy) mandelonitrile, optically active o-trimethylsilyloxymandelonitrile, optically active o-triethylsilyloxymandelonitrile, optically active o-tripropylsilyloxymandelonitrile, optically active o-(tert-butyldimethylsilyloxy)mandelonitrile, optically active o-naphthyloxymandelonitrile, optically active o-(4-methylphenoxy)mandelonitrile, optically active o-(2-methylphenoxy)mandelonitrile, optically active o-(2,4-dimethylphenoxy)mandelonitrile, optically active o-(2,4-di-tert-butylphenoxy)mandelonitrile, optically active o-(4-methoxyphenoxy)mandelonitrile, optically active o-(4-ethoxyphenoxy)mandelonitrile, optically active o-(2-fluorophenoxy)mandelonitrile, optically active o-(4-fluorophenoxy)mandelonitrile, optically active o-pentafluorophenoxy-mandelonitrile, optically active o-(2,6-dimethylphenoxymethyl)-p-(methoxymethyl)mandelonitrile, optically active o-(2,6-dimethylphenoxymethyl)-p-(methylthiomethyl)mandelonitrile, optically active o-(2,6-dimethylphenoxymethyl)-p-(phenylthiomethyl) mandelonitrile, optically active o-(2,6-dimethylphenoxymethyl)-p-trifluoromethoxymandelonitrile, optically active o-(2,6-dimethylphenoxymethyl)-p-pentafluoroethoxymandelonitrile, optically active o-(2,6-dimethylphenoxymethyl)-p-acetoxymandelonitrile, optically active o-(2,6-dimethylphenoxymethyl)-p-benzoyloxymandelonitrile, optically active o-(2,6-dimethylphenoxymethyl)-p-trimethylsilyloxymandelonitrile, optically active o-(2,6-dimethylphenoxymethyl)-p-triethylsilyloxymandelonitrile, optically active o-(2,6-dimethylphenoxymethyl)-p-(tert-butyldimethylsilyloxy) mandelonitrile, optically active o-(2,6-dimethylphenoxymethyl)-p-phenoxy-mandelonitrile, and optically active o-(2,6-dimethylphenoxymethyl)-p-pentafluorophenoxy-mandelonitrile.

EXAMPLES

The present invention will be described further in detail by examples below, but the present invention is not limited to these examples. The content was calculated based on the result of a high performance liquid chromatography internal standard method. The enantiomeric excess was measured by high performance liquid chromatography (column: SUMICHIRAL (registered trademark) OA-4900 manufactured by Sumika Chemical Analysis Service, Ltd., eluent: hexane/ethanol).

Example 1

Into a 30 mL three-necked flask was added 27 mg of aluminum chloride, 90 mg of 2, 6-bis(4-(S)-phenyloxazol-2-yl)pyridine and 1 mL of dichloromethane. The resultant mixture was adjusted to an internal temperature of 0° C. while stirring, to obtain a mixture containing an asymmetric complex. To the mixture was added 1 g of 2-(2,5-dimethylphenoxymethyl)benzaldehyde, 41 mg of trimethylsilyl cyanide and 3 mL of dichloromethane. The resultant mixture was stirred for 1 hour at an internal temperature of 0° C., then, 170 mg of hydrogen cyanide was dropped over a period of 3 hours. The resultant mixture was stirred for 2 hours at 0° C., to obtain a reaction mixture containing optically active o-(2,5-dimethylphenoxymethyl)mandelonitrile.

The conversion of 2-(2,5-dimethylphenoxymethyl)benzaldehyde: 95%

The enantiomeric excess of optically active o-(2,5-dimethylphenoxymethyl)mandelonitrile: 88% ee (R isomer)

Example 2

Into a 100 mL three-necked flask was added 27 mg of aluminum chloride, 90 mg of 2,6-bis(4-(S)-phenyloxazol-2-yl)pyridine and 5 mL of dichloromethane. The resultant mixture was adjusted to an internal temperature of 0° C. while stirring, to obtain a mixture containing an asymmetric complex. To the mixture was added 5 g of 2-(2,5-dimethylphenoxymethyl)benzaldehyde, 0.2 g of trimethylsilyl cyanide and 15 mL of dichloromethane. The resultant mixture was stirred for 1 hour at an internal temperature of 0° C., then, 0.83 g of hydrogen cyanide was dropped over a period of 3 hours. The resultant mixture was stirred for 14 hours at 0°0, to obtain a reaction mixture containing optically active o-(2,5-dimethylphenoxymethyl)mandelonitrile.

The conversion of 2-(2,5-dimethylphenoxymethyl)benzaldehyde: 51%

The enantiomeric excess of optically active o-(2,5-dimethylphenoxymethyl)mandelonitrile: 85%ee (R isomer)

Example 3

The same reaction as that in Example 1 was carried out except that 45 mg of trimethylsilyl chloride was used instead of 41 mg of trimethylsilyl cyanide in Example 1, thereby obtaining a reaction mixture containing optically active o-(2,5-dimethylphenoxymethyl)mandelonitrile.
The conversion of 2-(2,5-dimethylphenoxymethyl)benzaldehyde: 31%
The enantiomeric excess of optically active o-(2,5-dimethylphenoxymethyl)mandelonitrile: 50% ee (R isomer)

Example 4

The same reaction as that in Example 1 was carried out except that 67 mg of hexamethyldisilazane was used instead of 41 mg of trimethylsilyl cyanide in Example 1, thereby obtaining a reaction mixture containing optically active o-(2,5-dimethylphenoxymethyl)mandelonitrile.
The conversion of 2-(2,5-dimethylphenoxymethyl)benzaldehyde: 15%
The enantiomeric excess of optically active o-(2,5-dimethylphenoxymethyl)mandelonitrile: 68% ee (R isomer)

Example 5

The same reaction as that in Example 1 was carried out except that toluene was used instead of dichloromethane in Example 1, thereby obtaining a reaction mixture containing optically active o-(2,5-dimethylphenoxymethyl)mandelonitrile.
The conversion of 2-(2,5-dimethylphenoxymethyl)benzaldehyde: 95%
The enantiomeric excess of optically active o-(2,5-dimethylphenoxymethyl)mandelonitrile: 76% ee (R isomer)

Example 6

The same reaction as that in Example 1 was carried out except that 72 mg of 2,6-bis(4-(S)-isopropyloxazol-2-yl)pyridine was used instead of 90 mg of 2,6-bis(4-(S)-phenyloxazol-2-yl)pyridine in Example 1, thereby obtaining a reaction mixture containing optically active o-(2,5-dimethylphenoxymethyl)mandelonitrile.
The conversion of 2-(2,5-dimethylphenoxymethyl)benzaldehyde: 95%
The enantiomeric excess of optically active o-(2,5-dimethylphenoxymethyl)mandelonitrile: 82% ee (R isomer)

Example 7

The same reaction as that in Example 1 was carried out except that 2,6-bis(4-(R)-phenyloxazol-2-yl) pyridine was used instead of 2,6-bis(4-(S)-phenyloxazol-2-yl)pyridine in Example 1, thereby obtaining a reaction mixture containing optically active o-(2,5-dimethylphenoxymethyl)mandelonitrile.
The conversion of 2-(2,5-dimethylphenoxymethyl)benzaldehyde: 95%
The enantiomeric excess of optically active o-(2,5-dimethylphenoxymethyl)mandelonitrile: 84% ee (S isomer)

Example 8

Into a 100 mL three-necked flask was added 137 mg of aluminum chloride, 457 mg of 2,6-bis(4-(S)-phenyloxazol-2-yl)pyridine and 10 mL of dichloromethane. The resultant mixture was adjusted to an internal temperature of 0° C. while stirring, to obtain a mixture containing an asymmetric complex. To the mixture was added 5 g of 2-(2,5-dimethylphenoxymethyl)benzaldehyde, 0.21 g of trimethylsilyl cyanide and 15 mL of dichloromethane. The resultant mixture was stirred for 1 hour at an internal temperature of 0° C., then, 0.84 g of hydrogen cyanide was dropped over a period of 3 hours. The resultant mixture was stirred for 3 hours at 0° C., to obtain a reaction mixture containing o-(2,5-dimethylphenoxymethyl)mandelonitrile. The reaction mixture and 5 g of 3 wt % hydrochloric acid were mixed, allowed to stand still, then, an organic layer was separated. The resultant organic layer was washed with 10 g of 3 wt % hydrochloric acid, then, with 10 g of water, to obtain 42.1 g of of an organic layer containing optically active o-(2,5-dimethylphenoxymethyl)mandelonitrile.
The content of optically active o-(2,5-dimethylphenoxymethyl)mandelonitrile: 17.5 wt %
The yield of optically active o-(2,5-dimethylphenoxymethyl)mandelonitrile: 90.1%
The optical isomer excess of optically active o-(2,5-dimethylphenoxymethyl)mandelonitrile: 88% ee (R isomer)

Example 9

Into a 50 mL three-necked flask was added 96 mg of aluminum chloride, 0.32 g of 2,6-bis(4-(S)-phenyloxazol-2-yl) pyridine and 3 mL of dichloromethane. The resultant mixture was adjusted to an internal temperature of 0° C. while stirring, to obtain a mixture containing an asymmetric complex. To the resultant mixture was added 3 g of m-phenoxybenzaldehyde, 0.14 g of trimethylsilyl cyanide and 10 mL of dichloromethane. The resultant mixture was stirred for 1 hour at an internal temperature of 0° C., then, 0.57 g of hydrogen cyanide was dropped over a period of 3 hours. After completion of dropping, the resultant mixture was further stirred for 3 hours at an internal temperature of 0° C., to obtain a reaction mixture containing m-phenoxy-mandelonitrile. The reaction mixture and 5 g of 3 wt % hydrochloric acid were mixed, allowed to stand still, then, an organic layer was separated. The resultant organic layer was washed with 10 g of 3 wt % hydrochloric acid, then, with 10 g of water, to obtain 22.5 g of an organic layer containing m-phenoxy-mandelonitrile.
The content of optically active m-phenoxy-mandelonitrile: 16.6 wt %
The yield of optically active m-phenoxy-mandelonitrile: 89.3%
The enantiomeric excess of optically active m-phenoxy-mandelonitrile: 65% ee (R isomer)

Comparative Example 1

The same reaction as that in Example 1 was carried out except that trimethylsilyl cyanide was not used in Example 1, however, the reaction did not progress, and generation of optically active o-(2,5-dimethylphenoxymethyl)mandelonitrile could not be confirmed.

Industrial Applicability

The present invention is capable of obtaining an optically active cyanohydrin compound by using an asymmetric complex obtained from a cheap aluminum halide, thus, the present invention is industrially advantageous.

The invention claimed is:

1. A method of producing an optically active cyanohydrin compound represented by formula (3)

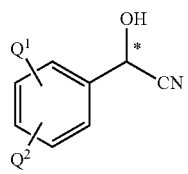
(3)

(wherein, $Q^1$ and $Q^2$ are as defined below, and * represents that the indicated carbon atom is the optically active center)
comprising reacting an aldehyde compound represented by formula (2)

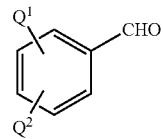
(2)

(wherein, $Q^1$ represents a hydrogen atom and $Q^2$ represents an alkyl group having 1 to 6 carbon atoms substituted by a 2.5-dimethylphenoxy group)
with hydrogen cyanide in the presence of a silyl compound and an asymmetric complex which is obtained by reacting an optically active pyridine compound represented by formula (1)

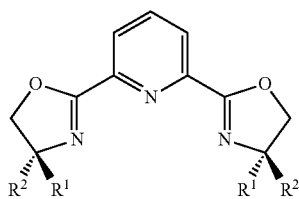
(1)

(wherein, $R^1$ and, $R^2$ and $R^2$ represent each independently a hydrogen atom, alkyl group having 1 to 6 carbon atoms, aryl group having 6 to 10 carbon atoms or aralkyl group having 7 to 11 carbon atoms, provided that $R^1$ and $R^2$ are not the same)
with an aluminum halide.

2. The production method according to claim 1 wherein the silyl compound is a trialkylsilyl cyanide compound.

3. The production method according to claim 1 wherein the silyl compound is trimethylsilyl cyanide.

4. The production method according to claim 1 wherein the aluminum halide is aluminum chloride.

5. The production method according to claim 1 wherein either $R^1$ or $R^2$ is a hydrogen atom and the other is an alkyl group having 1 to 6 carbon atoms, aryl group having 6 to 10 carbon atoms or aralkyl group having 7 to 11 carbon atoms.

6. The production method according to claim 1 wherein either $R^1$ or $R^2$ is a hydrogen atom and the other is an alkyl group having 1 to 6 carbon atoms or aryl group having 6 to 10 carbon atoms.

7. The production method according to claim 1 wherein the use amount of the asymmetric complex is 0.005 to 1 mol, in terms of aluminum atom, with respect to 1 mol of the aldehyde compound represented by formula (2).

8. The production method according to claim 1 wherein the use amount of the silyl compound is 0.01 to 0.5 mol with respect to 1 mol of the aldehyde compound represented by formula (2).

9. The production method according to claim 1 wherein the use amount of hydrogen cyanide is 1.1 to 3 mol with respect to 1 mol of the aldehyde compound represented by formula (2).

* * * * *